(12) United States Patent
Zeun et al.

(10) Patent No.: US 8,124,565 B2
(45) Date of Patent: Feb. 28, 2012

(54) METHOD OF PROTECTING A PLANT PROPAGATION MATERIAL, A PLANT, AND/OR PLANT ORGANS

(75) Inventors: Ronald Zeun, Basel (CH); Fredrik Cederbaum, Basel (CH); Michael Oostendorp, Basel (CH); Franz Brandl, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 566 days.

(21) Appl. No.: 12/278,645

(22) PCT Filed: Feb. 7, 2007

(86) PCT No.: PCT/EP2007/001035
§ 371 (c)(1),
(2), (4) Date: Nov. 25, 2008

(87) PCT Pub. No.: WO2007/090624
PCT Pub. Date: Aug. 16, 2007

(65) Prior Publication Data
US 2009/0221425 A1    Sep. 3, 2009

(30) Foreign Application Priority Data

Feb. 9, 2006 (EP) .................................. 06002628
Apr. 7, 2006 (EP) .................................. 06007368

(51) Int. Cl.
*A01N 43/40* (2006.01)
*A01N 43/56* (2006.01)
*A01P 3/00* (2006.01)

(52) U.S. Cl. ........ 504/100; 514/340; 514/406; 504/130; 504/139

(58) Field of Classification Search .................. 514/340, 514/406; 504/100, 130, 139
See application file for complete search history.

(56) References Cited

FOREIGN PATENT DOCUMENTS

| CN | 1280767 | | 1/2001 |
|---|---|---|---|
| CN | 1608467 | A | 4/2005 |
| CN | 1608469 | A | 4/2005 |
| EP | 1035122 | A | 9/2000 |
| WO | 2006/069715 | A | 7/2006 |
| WO | 2007/010036 | A | 1/2007 |

OTHER PUBLICATIONS

Derwent abstract 2005-598453; abstracting CN 1608467 (Oct. 2003).*
Derwent abstract 2005-598455; abstracting CN 1608469 (Oct. 2003).*
Webster's New World Dictionary, second college edition, The world Publishing Co., NY, 1972, p. 1127.*
Si, Naiguo et al, "Biological Activity and Application of a Novel Fungicide: SYP-Z048 (I)", (2004).
Si, Naiguo et al, "Biological Activity and Application of a Novel Fungicide: SYP-Z048 (II)", (2004).
Liu, Junli et al, "Biological Activity Against Tomato Leaf Mold and Application of a Novel Fungicide, SYP-Z048 (III)", (2004).

* cited by examiner

*Primary Examiner* — John Pak
(74) *Attorney, Agent, or Firm* — James Cueva

(57) ABSTRACT

A method of controlling or preventing pathogenic damage or pest damage in a plant propagation material, a plant, and/or plant organs that grow at a later point in time, which comprises applying on the plant propagation material a compound of formula (I) and stereoisomers, diastereomers, and agronomically acceptable salts thereof.

(I)

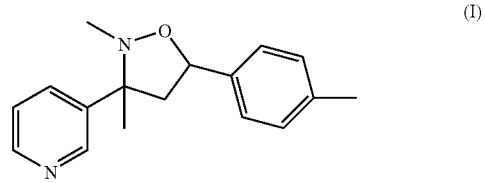

7 Claims, No Drawings

METHOD OF PROTECTING A PLANT PROPAGATION MATERIAL, A PLANT, AND/OR PLANT ORGANS

This application is a National Stage Entry under 35 USC §371 of International application serial number PCT/EP2007/001035, filed on Feb. 7, 2007, which claims priority to EP 06002628.3, filed on Feb. 9, 2006, and EP 06007368.1, filed Apr. 7, 2006, the contents of which are incorporated herein by reference.

The present invention relates to a method for using a defined compound in the control or prevention of pathogenic damage, in particular in a plant propagation material and plant organs that grow at a later point in time by applying the compound on to the plant propagation material, plant propagation material compositions thereof and combinations of such a compound with certain pesticides.

The treatment of plant propagation material is a targeted pesticide application which addresses the need for a reduction of environmental and worker exposure compared to foliar or soil pesticide applications.

Pesticidal active ingredients and combinations thereof for controlling pathogens and pests in plant propagation materials and plant organs that grow at a later point in time are described in the literature. The biological properties of those known compounds and combinations are not entirely satisfactory in the areas of pathogenic control, phytotoxicity, and environmental and worker exposure, for example. In particular, in the instance a pathogen has become, or risks becoming resistant to the previously known combinations, improved methods of control or prevention are sought.

There is a continuing need to provide pesticidal compositions, which provide improved, for example, biological properties, especially for controlling pathogens.

EP1035122 discloses a number of heterocyclic substituted isoxazolidines compounds as having biological properties for fungi control.

It has now been found that a certain substituted isoxazolidine compound has unexpectedly good activity when applied onto a plant propagation material. Accordingly, in a first aspect, the present invention provides a method of controlling or preventing pathogenic damage or pest damage in a plant propagation material, a plant, part of a plant and/or plant organs that grow at a later point in time, which comprises applying on the plant propagation material a compound of formula I

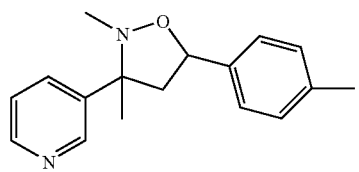

I and stereoisomers, diastereomers, and agronomically acceptable salts thereof.

In a second aspect, the present invention provides a method of protecting a plant propagation material, a plant, part of a plant and/or plant organs that grow at a later point in time against pathogenic damage or pest damage by applying to the plant propagation material a compound defined in the first aspect.

The invention also relates to a plant propagation material treated with the compound defined in the first aspect.

The present invention also relates to a method which comprises (i) treating a plant propagation material, such as a seed, with a compound as defined in the first aspect, and (ii) planting or sowing the treated propagation material, wherein the compound protects against pathogenic damage or pest damage of the treated plant propagation material, parts of plant, plant organs and/or plant grown from the treated propagation material.

Further, the present invention concerns a method which comprises (i) treating a plant propagation material, such as a seed, with a compound as defined in the first aspect, and (ii) planting or sowing the treated propagation material, and (iii) achieving protection against pathogenic damage or pest damage of the treated plant propagation material, parts of plant, plant organs and/or plant grown from the treated propagation material.

In an embodiment of any aspect of the invention, the compound has a structure selected from

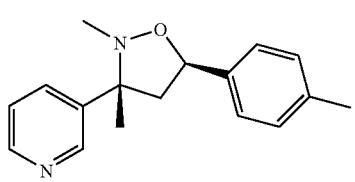

Ia

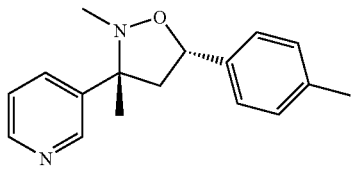

Ib

In a preferred embodiment, a stereoisomeric or diastereomeric mixture of compound of formula I is applied on the plant propagation material.

According to the instant invention, a "stereoisomeric or diastereomeric mixture" of two stereoisomers or diastereomers or a "stereoisomeric or diastereomeric compound" means a mixture of two stereoisomers or diastereomers in a ratio from 1:10 to 10:1. Accordingly, ratio of compound of formula Ia to compound of formula 1b can be from 1:10 to 10:1, preferably 1:5 to 5:1, more preferably 3:1 to 1:3, such as 2.5:1 to 1.5:1.

In a further aspect of the invention, the compound of formula 1 is present in the form of a plant propagation material, preferably seed, treatment composition, wherein the composition optionally further comprises one or more customary formulation auxiliaries.

In an embodiment of each aspect, a combination comprising the compound defined in the first aspect and one or more pesticides are applied on the plant propagation material, in any desired sequence or simultaneously.

In the event a combination is used, the compound of formula I and one or more pesticides are present in the form of a plant propagation material, preferably seed, treatment composition, wherein the composition optionally further comprises one or more customary formulation auxiliaries.

Examples of pesticides include fungicides, bactericides, insecticides, acaricides and nematicides. A preferred pesticide for use in combination with the compound of formula I is a fungicide.

Suitable examples of fungicides are fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, a manganese compound (such as mancozeb, maneb), a compound of formula A

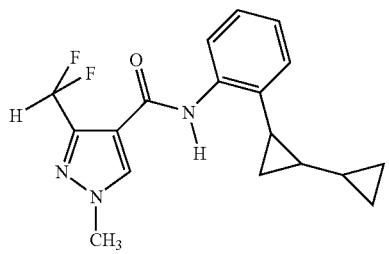

A or a tautomer of such a compound, and a compound of formula B

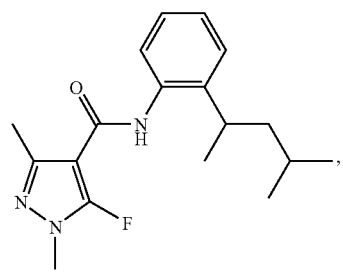

or a tautomer of such a compound.

In the instance a an insecticide, acaricide and/or nematcide, is also used in the present invention the biological spectrum of the combination is broadened to such an extent that the combination demonstrates activity against damage caused by a pest, such as an animal pest.

Suitable examples are thiamethoxam, imidacloprid, clothianidin, lamda-cyhalothrin, tefluthrin, β-cyfluthrin, permethrin, abamectin, fipronil, and spinosad.

In an aspect of the invention, the present invention also provides a combination comprising a compound of formula I, as defined the first aspect, and one or more defined pesticides. The combination is suitable for controlling or preventing pathogenic damage or pest damage in a plant propagation material, a plant, and/or plant organs that grow at a later point in time, which comprises applying on the plant, part of the plant or surroundings thereof, or plant propagation material thereof, the combination, in any desired sequence or simultaneously.

The compound of formula A can occur in different stereoisomeric forms, which are described in formulae $A_I$, $A_{II}$, $A_{III}$ and $A_{IV}$:

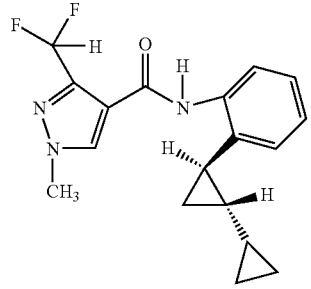

$A_I$

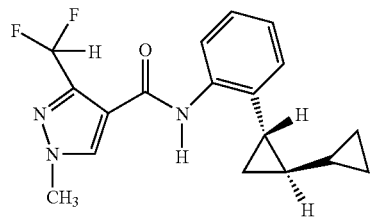

$A_{II}$

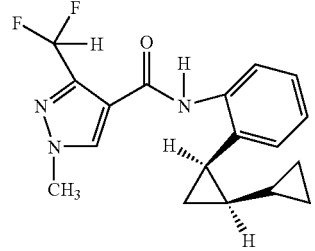

$A_{III'}$

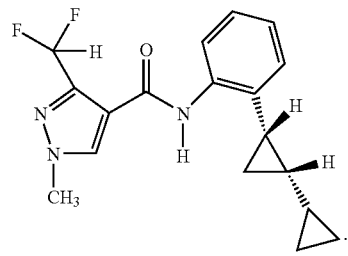

$A_{IV}$

The invention covers all such stereoisomers and mixtures thereof in any ratio with a combination of compound of formula I.

In an embodiment, compound A is a compound of the formula Aa (trans)

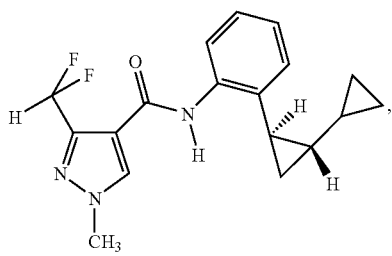

(Aa)

which represents a compound of formula $A_I$, a compound of formula $A_{II}$ or a mixture in any ratio of a compound of formula $A_I$ and a compound of formula $A_{II}$.

In an embodiment, compound A is a compound of the formula Ab (cis)

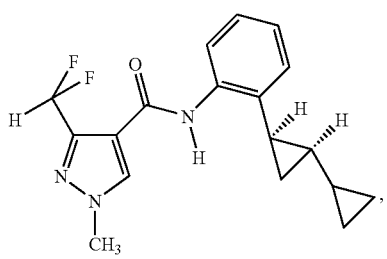

(Ab)

which represents a compound of formula $AI_{III}$, a compound of formula $A_{IV}$ or a mixture in any ratio of a compound of formula $A_{III}$ and a compound of formula $A_{IV}$.

In a preferred embodiment compound A is a racemic mixture of compound formula A, wherein the weight ratio of racemic compounds of formula Aa, which represent a racemic mixture of compounds of formula $A_I$ and compounds of formula $A_{II}$, to racemic compounds of formula Ab, which represent a racemic mixture of compounds of formula $A_{III}$ and compounds of formula $A_{IV}$, is from 1:1 to 100. Suitable examples of weight ratios of compound of formula Aa to Ab in a racemic mixture are 1:1, 2:1, 3:1, 4:1, 5:1, 6:1, 7:1, 8:1, 9:1, 10:1, 20:1, 50:1 or 100:1. Preference is given to ratios from 2:1 to 100:1, more preferably 4:1 to 10:1.

In an especially preferred embodiment compound A is a racemic mixture, wherein the content of racemic compound of formula Aa, which represent a racemic mixture of compounds of formula $A_I$ and compounds of formula $A_{II}$, is from 65 to 99% by weight.

Details (e.g., structure, chemical name, commercial names, etc) of each of the pesticides with a common name can be found in the e-Pesticide Manual, version 3.1, 13th Edition, Ed. CDC Tomlin, British Crop Protection Council, 2004-05.

The compound of formula I is described in EP-1-035-122 and is registered under CAS 847749-37-5, CAS-291771-99-8 and CAS-291771-83-0.

The compound of formula A (including the different stereoisomeric forms) and its manufacturing processes starting from known and available compounds are described in WO 03/074491.

Details of compound of formula B are disclosed in WO 03/010149 and WO 05/58839.

Controlling, preventing or protecting and its inflections, within the context of the present invention, mean reducing any undesired effect, such as pathogenic, such as phytopathogenic, especially fungi, infestation or attack of, and pathogenic damage or pest damage on, a plant, part of the plant or plant propagation material to such a level that an improvement is demonstrated.

The compound defined in the first aspect and combinations thereof can have very advantageous properties for protecting plants against (i) pathogenic, such as phytopathogenic, especially fungi, attack or infestation, which result in a disease and damage to the plant and/or (ii) pest attack or damage in the instance a pesticide that is, for example, an insecticide, acaricide and/or nematcide is also present; the present invention can control or prevent pathogenic damage and/or pest damage on a seed, parts of plant and/or plant grown from the treated seed.

These properties can be for example the unexpected enhanced action resulting in lower pathogenic damage and/or pest damage, lower rates of application, or a longer duration of action. In the instance of agriculture, the enhanced action is found to show an improvement in the growing characteristics of a plant by, for example, higher than expected control of the pathogenic infestation and/or pest damage.

The improvement in the growing (or growth) characteristics of a plant can manifest in a number of different ways, but ultimately it results in a better product of the plant. It can, for example, manifest in improving the yield and/or vigour of the plant or quality of the harvested product from the plant, which improvement may not be connected to the control of diseases and/or pests.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or, improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

Accordingly, the present invention also provides a method of improving the growing characteristics of a plant, which comprises applying to a plant propagation material the compound of the first aspect or a combination thereof. In the event a combination is used, the application of the compound of formula I and one or more pesticides can be in in any desired sequence or simultaneously.

When the compound of formula I is used in combination with one or more pesticides, a synergistically enhanced activity may be observed.

Accordingly, the invention makes available a combination comprising a compound of formula I and one or more of a pesticide selected from fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, a manganese compound (such as mancozeb, maneb), a compound of formula A, compound of formula B, thiamethoxam, imidacloprid, clothianidin, lamda-cyhalothrin, tefluthrin, β-cyfluthrin, permethrin, abamectin, fipronil, and spinosad.

In an embodiment, a combination comprising a compound of formula I and a compound of formula A; compound of formula I and a compound of formula B; a compound of formula I and penthiopyrad; a compound of formula I and triticonazole; a compound of formula I and prothioconaziole; a compound of formula I and fluoxastrobin; a compound of formula I and fluquinconazole; a compound of formula I and flutriafol, a compound of formula I and guazatine; a compound of formula I and difenoconazole; a compound of formula I and fludioxonil; a compound of formula I and prochloraz; a compound of formula I and ipconazole; a compound of formula I and thiamethoxam, a compound of formula I and imdiacloprid, a compound of formula I and chlothianidin; a compound of formula I and fipronil, a compound of formula I and abamectin, a compound of formula I and tefluthrin, a compound of formula. I and lambda cyhalothrin, a compound of formula I and beta-cyfluthrin, a compound of formula I and cyproconazole; a compound of formula I and azoxystrobin; a compound of formula I and metalaxyl; a compound of formula I and mefenoxam; a compound of formula I and thiram; a compound of formula I and captan; a compound of formula I and spinosad; a compound of formula I and permethrin; or a compound of formula I and tebuconazole; is preferred according to the invention.

In an embodiment, a combination can comprise a compound of formula I, a compound of formula A, and a compound selected from fludioxonil, metalaxyl, mefenoxam, cyprodinil, azoxystrobin, tebuconazole, difenoconazole and thiabendazole.

In a further embodiment, a combination comprising a compound of formula I, an insecticide selected from thiamethoxam, imidacloprid, clothianidin, fipronil, abamectin, tefluthrin, and beta-cyfluthrin, and boscalid or epoxyconazole or tolylfluanid; a compound of formula I, an insecticide selected from thiamethoxam, imidacloprid, clothianidin, fipronil, abamectin, tefluthrin and beta-cyfluthrin, and azoxystrobin; a compound of formula I, an insecticide selected from thiamethoxam, imidacloprid, clothianidin, fipronil, abamectin, tefluthrin and beta-cyfluthrin, and fludioxonil, a compound of formula I, an insecticide selected from thiamethoxam, imidacloprid, clothianidin, fipronil, abamectin, tefluthrin and beta-cyfluthrin, and mefenoxam, a compound of formula I, an insecticide selected from thiamethoxam, imidacloprid, clothianidin, fipronil, abamectin, tefluthrin and beta-cyfluthrin, and compound of formula A; a compound of formula I, an insecticide selected from thiamethoxam, imidacloprid, clothianidin, fipronil, abamectin, tefluthrin and beta-cyfluthrin, and prochloraz; a compound of formula I, an insecticide selected from thiamethoxam, imidacloprid, clothianidin, fipronil, abamectin, tefluthrin and beta-cyfluthrin, and prothioconazole; a compound of formula I, an insecticide selected from thiamethoxam, imidacloprid, clothianidin, fipronil, abamectin, tefluthrin and beta-cyfluthrin, and fluoxastrobin; a compound of formula I, an insecticide selected from thiamethoxam, imidacloprid, clothianidin, fipronil, abamectin, tefluthrin and beta-cyfluthrin, and penthiopyrad; a compound of formula I, an insecticide selected from thiamethoxam, imidacloprid, clothianidin, fipronil, abamectin, tefluthrin and beta-cyfluthrin, and ipconazole, is advantageous.

The compound of formula I and combinations thereof are effective against phytopathogenic fungi, especially occurring in plants, including seedborne fungi and belong to the following classes: Ascomycetes (e.g. *Penicillium, Gaeumannomyces graminis*); Basidiomycetes (e.g. the genus *Hemileia, Rhizoctonia, Puccinia*); Fungi imperfecti (e.g. *Botrytis, Helminthosporium, Rhynchosporium, Fusarium, Septoria, Cercospora, Alternaria, Pyricularia* and *Pseudocercosporella herpotrichoides*); Oomycetes (e.g. *Phytophthora, Peronospora, Bremia, Pythium, Plasmopara*); Zygomycetes (e.g., *Rhizopus* spp.). A combination is especially effective against *Alternaria* spp., *Ascochyta* spp., *Aspergillus* spp., *Claviceps purpurea, Cochliobolus* spp., *Colletotrichum* spp., *Diplodia maydis, Erysiphe graminis, Fusarium* spp. (such as *Fusarium culmorum, Fusarium oxysporum, Fusarium solani, Fusarium graminearum* and *Fusarium moniliforme, Fusarium subglutinans*), *Gaeumannomyces graminis, Giberella fujikuroi, Giberella zeae, Helminthosporium* spp. (such as *Helminthosporium graminearum, Helminthosporium oryzae, Helminthosporium solani*), *Monographella nivalis, Penicillium* spp., *Puccinia* spp., *Pyrenophora* spp. (such as *Pyrenophora graminea*), *Peronosclerospora* spp., *Peronspora* spp., *Phakopsora pachyrhizi, Phythium* spp., *Phoma* spp., *Phomopsis* spp., *Rhizoctonia* spp. (such as *Rhizoctonia cerealis, Rhizoctonia solani*), *Septoria* spp., *Pseudocercosporella* spp., *Tilletia* spp., *Rhizopus* spp., *Thielaviopsis basicola, Typhula* spp., *Ustilago* spp., *Sphacelotheca* spp. (e.g. *Spacelotheca reilliani*), *Thanatephorus cucumeris*, and *Verticillium* spp.

In the event a combination of the invention also includes a pesticide other than fungicide (such as abamectin, imidacloprid, tefluthrin, lambda-cyhalothrin) then the pesticide spectrum of the combination is broadened to include pest control, such as control of pests selected from Nematoda, Insecta and Arachnida. In that instance, the combination can also be applied on the pest to control or prevent pest damage and protect the desired material (e.g. plant propagation material, plant and parts of plant) from pest damage. Examples of pests include:

from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia* spp., *Cryptophlebia leucotreta, Crysodeixis includens, Cydia* spp., *Diatraea* spp., *Diparopsis castanea, Earias* spp., *Elasmopalpus* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Coleoptera, for example, *Agriotes* spp., *Anthonomus* spp., *Atomaria linearis, Ceutorhynchus* spp., *Chaetocnema tibialis, Cosmopolites* spp., *Curculio* spp., *Dermestes* spp., *Diabrotica* spp., *Epilachna* spp., *Eremnus* spp., *Gonocephalum* spp., *Heteronychus* spp., *Leptinotarsa decemlineata, Lissorhoptrus* spp., *Melolontha* spp.,

*Orycaephilus* spp., *Otiorhynchus* spp., *Phlyctinus* spp., *Phyllotreta* spp., *Popillia* spp., *Protostrophus* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp.;

from the order Orthoptera, for example, *Blatta* spp., *Blattella* spp., *Gryllotalpa* spp., *Leucophaea maderae*, *Locusta* spp., *Periplaneta* spp. and *Schistocerca* spp.;

from the order Isoptera, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Mallophaga, for example, *Damalinea* spp. and *Trichodectes* spp.;

from the order Thysanoptera, for example, *Frankliniella* spp., *Hercinothrips* spp., *Taeniothrips* spp., *Thrips palmi*, *Thrips tabaci* and *Scirtothrips aurantii;* from the order Heteroptera, for example, *Dichelops melacanthus*, *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Triatoma* spp.;

from the order Homoptera, for example, *Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri;* from the order Hymenoptera, for example, *Acromyrmex*, *Athalia rosae*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.;

from the order Diptera, for example, *Antherigona soccata*, *Bibio hortulanus*, *Ceratitis* spp., *Chrysomyia* spp., *Culex* spp., *Cuterebra* spp., *Dacus* spp., *Delia* spp., *Drosophila melanogaster*, *Liriomyza* spp., *Melanagromyza* spp., *Orseolia* spp., *Oscinella frit*, *Pegomyia hyoscyami*, *Phorbia* spp., *Rhagoletis pomonella*, *Sciara* spp.;

from the order Acarina, for example, *Acarus siro*, *Aceria sheldoni*, *Aculus schlechtendali*, *Amblyomma* spp., *Argas* spp., *Brevipalpus* spp., *Bryobia praetiosa*, *Calipitrimerus* spp., *Chorioptes* spp., *Dermanyssus gallinae*, *Eotetranychus carpini*, *Eriophyes* spp., *Hyalomma* spp., *Olygonychus pratensis*, *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Tarsonemus* spp. and *Tetranychus* spp.; and from the class Nematoda, for example, the species of *Meloidogyne* spp. (for example, *Meloidogyne incoginita* and *Meloidogyne javanica*), *Heterodera* spp. (for example, *Heterodera glycines*, *Heterodera schachtii*, *Heterodera avenae* and *Heterodera trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonlaimus* spp., *Criconemella* spp., *Criconemoides* spp. *Ditylenchus* spp., *Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

The compound of formula I and combinations thereof can be formulated for a particular use. Preferably, the compound of formula I and combination thereof can be formulated for protecting cultivated plants or their propagation materials. In an embodiment, the combination of the invention can be applied to the plant in a conventional manner, such as foliar spray. Advantageously, the combinations are formulated for plant propagation material, preferably seed, treatment applications for controlling or preventing damage by pests and/or pathogens, which are found in agriculture and forestry, and can particularly damage the plant in the early stages of its development.

Further, the present invention also envisages soil application of the combinations of the invention to control the soil-dwelling pests and/or soil-borne pathogens. Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods.

The benefit from the invention can also be achieved either by (i) treating plant propagation material with a compound of formula I or a combination thereof or (ii) applying to the locus where control is desired, generally the planting site, the compound of formula I or a combination thereof, or both (i) and (ii).

The term "plant propagation material" is understood to denote all the generative parts of the plant, such as seeds, which can be used for the multiplication of the latter and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pathogenic and/or pest damage protection achieved by the application of the combination on to the plant propagation material. In an embodiment, certain parts of plant and certain plant organs that grow at later point in time can also be considered as plant propagation material, which can themselves be applied (or treated) with the combination; and consequently, the plant, further parts of the plant and further plant organs that develop from the treated parts of plant and treated plant organs can also benefit from the pathogenic and/or pest damage protection achieved by the application of the combination on to the certain parts of plant and certain plant organs.

Methods for applying or treating pesticidal active ingredients and mixtures thereof on to plant propagation material, especially seeds, are known in the art, and include dressing, coating, pelleting and soaking application methods of the propagation material.

The active ingredients can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In a preferred embodiment, the compound of formula I and a combination thereof is applied or treated on to the plant propagation material by a method such that the germination is not induced; generally seed soaking induces germination because the moisture content of the resulting seed is too high. Accordingly, examples of suitable methods for applying (or treating) a plant propagation material, such as a seed, is seed dressing, seed coating or seed pelleting and alike.

It is preferred that the plant propagation material is a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the active ingredients and adherence thereof to the seeds is desired during propagation material treatment. Treatment could vary from a thin film (dressing) of the formulation containing the active ingredient(s) on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the active ingredients in the combination are adhered on to the seed and therefore available for pest and/or disease control.

The treated seeds can be stored, handled, sowed and tilled in the same manner as any other active ingredient treated seed.

The compound of formula I and combinations thereof according to the present invention is suitable for plants of the crops: cereals (wheat, barley, rye, oats, corn, rice, sorghum, triticale and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, onions, tomatoes, potatoes, paprika); as well as ornamentals (flowers, shrubs, broad-leaved trees and evergreens, such as conifers). Especially suitable are wheat, barley, rye, oats, corn and soybean, triticale.

Suitable target crops also include transgenic crop plants of the foregoing types. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The weight ratio of a compound of formula I with a pesticide is selected as to give the desired, for example, synergistic, action. In general, the weight ratio would vary depending on the specific pesticide and how many pesticides are present in the combination. Generally, the weight ratio between any two active ingredients is from 100:1 to 1:100, preferably from 75:1 to 1:75, more preferably, 50:1 to 1.50, especially 25:1 to 1:25, advantageously 10:1 to 1:10.

The rates of application (use) of the compound of formula I alone or in combination with one or more pesticides vary, for example, according to type of use, type of crop, the specific active ingredients in the combination, type of plant propagation material but is such that the active ingredients in the combination is an effective amount to provide the desired enhanced action (such as disease or pest control) and can be determined by trials.

Generally for seed treatment, application rates can vary from 0.5 to 1000 g/100 kg of seeds of active ingredients.

Suitable seed treatment application rates of (I) a compound of formula I tend to be 1-80, preferably 2-40, more preferably 2.5-20, g/100 kg, of seeds, and if one or more pesticides are also present, then rates tend to 1-700, preferably 2-550, more preferably 2-450, g/100 kg. The plant propagation material treated by a compound of formula I or combination thereof of the present invention are, therefore, resistant to disease and/or pest damage; accordingly, the present invention also provides a pathogenic and/or pest resistant plant propagation material which is treated with compound of formula I or the combination thereof and consequently at least the active ingredients thereof are adhered on the propagation material, such a seed.

The seed treatment composition comprising a compound of formula I or combination thereof can also comprise or may be applied together and/or sequentially with further active compounds. These further compounds can be other pesticidal active ingredients, fertilizers or micronutrient donors or other preparations that influence plant growth, such as inoculants and plant inducers.

A single pesticidal active ingredient may have activity in more than area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

The combination of the present invention may be mixed with other pesticides, such as fungicides, insecticides and nematicides.

Suitable examples of fungicides, insecticides and nematicides include triazole derivatives, strobilurins, carbamate (including thiocarbamate), benzimidazoles (thiabendazole), N-trihalomethylthio compounds (captan), substituted benzenes, carboxamides, phenylamides and phenylpyrroles, and mixtures thereof; and neonicotinoids, avermectins, carbamates and pyrethroids.

The compound of formula I and the pesticide(s) may be used either in pure form, i.e., as a solid active ingredient, for example, in a specific particle size, or preferably together with at least one of the auxiliary (also known as adjuvants) customary in formulation technology, such as extenders, e.g., solvents or solid carriers, or surface-active compounds (surfactants), in the form of a formulation, in the present invention. Generally, the compound and pesticide(s) are in the form of a formulation composition with one or more of customary formulation auxiliaries.

In an embodiment, the present invention is a method comprising:
(a) treating plant propagation material with a compound of formula I or a combination thereof,
(b) germinating or growing said plant propagation material to produce a plant,
(c) harvesting plant material from said plant, and
(d) achieving a reduction in the mycotoxin contamination of (a) the plant grown from the treated plant propagation material and/or (b) harvested plant material.

The mycotoxin contamination is preferably caused by fungi, such as one or more *Fusarium* species, infestation of the plant propagation material.

In an embodiment, the mycotoxin is one or more of a fumonisin and trichothecene, preferably the mycotoxin is deoxynivalenol and/or zearalenon.

The method for reducing mycotoxin contamination of a plant and/or harvested plant material is suitable for a number of useful crops including, but not limited to cereals (wheat, barley, rye, oats, maize (or corn), rice, sorghum and related crops), leguminous plants (beans, lentils, peas, soybeans, peanuts and related crops), oil plants (rape, mustard, sunflowers and related plants), cucumber plants (marrows, cucumbers, melons and related plants), vegetables (spinach, lettuce, asparagus, cabbages, carrots, eggplants, onions, pepper, tomatoes, potatoes, paprika and related plants). Harvested plant material obtained from plants treated using the method of the invention will have less mycotoxin contamination than harvested plant material from untreated plants. In an embodiment, the crop is one producing a product for human consumption, such as small grain cereals, maize, oats, and peanuts; preferably the crop is selected from maize and wheat.

In a particular embodiment of the invention, plant or harvested plant material has at least 10% less mycotoxin, more preferable at least 20% less mycotoxin, more preferably at least 30% less mycotoxin, more preferably at least 40% less mycotoxin, more preferably at least 50% less mycotoxin, more preferably at least 60% less mycotoxin, more preferably at least 70% less mycotoxin and more preferably at least 80% less mycotoxin contamination than harvested plant material from untreated plants. The plant propagation material treatment with the compound of formula I or defined combinations thereof of the invention preferably provide a reduction of between 20 to 60, more preferably between 30 to 50; %, in mycotoxin compared to treatments by other fungicides.

Therefore, a compound of formula I or combination thereof is normally used in the form of formulations. The compound of formula I and the pesticide(s) making-up the combination can be applied to the locus where control is desired either simultaneously or in succession at short interval, for example on the same day, if desired together with further carriers, surfactants or other application-promoting adjuvants customarily employed in formulation technology. In a preferred embodiment, the combination is applied simultaneously.

In the event combination is applied simultaneously in the present invention, they may be applied as a composition, in which case the compound of formula I and the pesticide(s) can be obtained from a separate formulation source and mixed together (known as a tank-mix, ready-to-apply, spray broth, or slurry), optionally with other pesticides, or they can be obtained as single formulation mixture source (known as a pre-mix, concentrate, formulated compound (or product)), and optionally mixed together with other pesticides.

In an embodiment, the combination of the present invention is applied as a composition.

In a preferred embodiment of the invention, the composition is a pre-mix composition (or mixture).

Examples of foliar formulation types for pre-mix compositions are
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The formulations are prepared in known manner, e.g., by homogeneously mixing and/or grinding the active ingredients with extenders, e.g., solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g., for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g., especially dolomite or pulverized plant residues.

Depending upon the nature of the active ingredient compounds to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g., phosphatidylethanolamine, phosphatidylserine, phosphatidylglycerol and lysolecithin.

Generally, a tank-mix formulation for foliar or soil application comprises 0.1 to 20%, especially 0.1 to 15%, active ingredient compounds, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, active ingredient compounds, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, active ingredient compounds, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, active ingredient compounds, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The Examples which follow serve to illustrate formulations according to the invention, "active ingredient" denoting a compound of formula I or a combination thereof with another pesticide(s).

FORMULATION EXAMPLES

| Wettable powders | a) | b) | c) |
| --- | --- | --- | --- |
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
| --- | --- |
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredient | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
| --- | --- |
| Active ingredient | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
| --- | --- |
| Active ingredient | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
| --- | --- |
| active ingredient | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
| --- | --- |
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

In a preferred embodiment, each of the combination of the present invention is a plant propagation material, preferably seed, treating composition.

Using such formulations either straight or diluted plant propagation material can be treated and protected against damage, for example, from pathogen(s), by, for example, spraying, pouring or immersing.

The compound of formula I and combinations thereof are distinguished by the fact that they are especially well tolerated by plants and are environmentally friendly.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples are given by way of illustration and not by way of limitation of the invention.

BIOLOGICAL EXAMPLES

Example A

A-1. *Pyrenophora graminea*/Barley (Stripe Disease on Barley)

After application of the formulated seed treatment onto *P. graminea*-infected seeds of winter barley the seeds are sown in trays filled with field soil. The trays are kept in a growth room for 3 weeks at 4° C. After this period the trial is transferred to a greenhouse where a temperature of 12° C. and a 14 hr light period is provided. The following assessments are made: emergence count, final stand count, number of infected plants.

Compound of formula I @ 20 g/100 kg: 100% activity

A-2. *Rhizoctonia solani*/Cotton (Damping Off on Cotton)

A defined amount of mycelium of *R. solani* is blended with soil and trays are filled with the inoculated soil. The formulated test compounds are applied to cotton seeds. The treated cotton seeds are then sown into the inoculated soil. Until germination the test is stored at 20° C. and a rel. humidity of 90% in the dark. After germination the test is transferred to 25° C. and a rel. humidity of 70% with a photoperiod of 14 h. The evaluation is done by counting the emerged cotton plants and the number of emerged and diseased plants.

Compound of formula I @ 200 g/100 kg: 70% activity

A-3. *Fusarium graminearum*/Corn

A defined amount of mycelium of *F. graminearum* is blended with soil and trays are filled with the inoculated soil. The formulated test compounds are applied to corn seeds (cv. Magister). The treated corn seeds are then sown into the inoculated soil. Until germination the test is stored at 10° C. and a rel. humidity of 80% in the dark. After germination the test is transferred to 13° C. and a rel. humidity of 70% with a photoperiod of 14 h. The evaluation is done by counting the emerged plants.

Compound of formula I @ 20 g/100 kg: 100% activity

Example B

A synergistic effect exists whenever the action of an active ingredient combination is greater than the sum of the actions of the individual components. The following illustrates the invention in respect of Compound of formula I and Compound of formula A—

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect.

Example B-1

Activity Against *Pyrenophora graminea* on Barley

Fungal Growth Assay

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is measured photometrically after 72 hrs. The fungicide interactions in the combinations are calculated according to COLBY method.

| Control of *Pyrenophora graminea* | | | | |
|---|---|---|---|---|
| Dosage in mg active ingredient/ liter final medium ppm) | | | | |
| Compd I in ppm | Compd A in ppm | Compd A + Compd in ppm/ppm | Observed control in % (% $C_{obs}$) | Expected control in % (% $C_{exp}$) |
| — | 1 | — | 0 | — |
| — | 0.25 | — | 0 | — |
| 0.5 | — | — | 62.3 | — |
| | | 1/0.5 | 71.9 | 62.3 |
| | | 0.25/0.5 | 73.4 | 62.3 |

Example B-2

Activity Against *Gäumannomyces graminis* on Wheat

Fungal Growth Assay

Mycelial fragments of a newly grown culture of the fungus, are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is measured photometrically after 72 hrs. The fungicide interactions in the combinations are calculated according to COLBY method.

| Control of *Gäumannomyces graminis* | | | | |
|---|---|---|---|---|
| Dosage in mg active ingredient/ liter final medium ppm) | | | | |
| Compd I in ppm | Compd A in ppm | Compd A + Compd in ppm/ppm | Observed control in % (% $C_{obs}$) | Expected control in % (% $C_{exp}$) |
| — | 0.5 | — | 74.8 | — |
| 0.25 | — | — | 26.0 | — |
| | | 0.5/0.25 | 86.9 | 74.8 |

Example B-3

Activity Against *Fusarium graminearum*

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is determined photometrically after 48 hrs. The fungicide interactions in the combinations are calculated according to COLBY method.

| Control of *Fusarium graminearum* | | | | |
|---|---|---|---|---|
| Dosage in mg active ingredient/ liter final medium ppm) | | | | |
| Compd I in ppm | Compd A in ppm | Compd A + Compd I in ppm/ppm | Observed control in % (% $C_{obs}$) | Expected control in % (% $C_{exp}$) |
| — | 0.25 | — | 7.8 | — |
| — | 0.125 | — | 8.4 | — |
| — | 0.0625 | — | 2.4 | — |
| — | 0.03125 | — | 1.6 | — |
| 0.25 | — | — | 12.5 | — |
| 0.125 | — | — | 4.4 | — |
| 0.0625 | — | — | 3.5 | — |
| 0.03125 | — | — | 0 | — |
| | | 0.125/0.03125 | 13.3 | 8.4 |
| | | 0.25/0.125 | 16.7 | 11.9 |
| | | 0.0625/0.0625 | 10.4 | 5.9 |
| | | 0.0625/0.125 | 13.8 | 6.7 |
| | | 0.0625/0.25 | 18.2 | 14.6 |
| | | 0.03125/0.125 | 8.2 | 5.9 |

The invention claimed is:
1. A composition comprising:
a compound of formula I

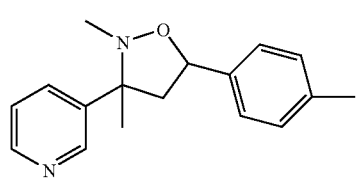

and stereoisomers, diastereomers, and agronomically acceptable salts thereof, and a compound of formula A

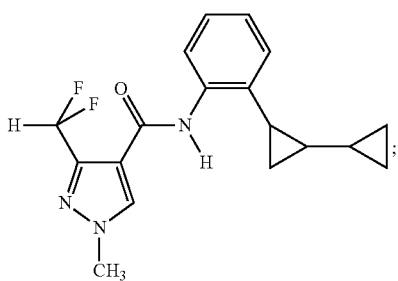

and optionally one or more customary formulation auxiliaries.

2. A plant propagation material treated with the composition defined in claim 1.

3. A composition according to claim 1, wherein the weight ratio of the compound of formula I to the compound of formula A is from 100:1 to 1:100.

4. A composition according to claim 1, wherein the weight ratio of the compound of formula I to the compound of formula A is from 10:1 to 1:10.

5. A composition according to claim 1, wherein the weight ratio of the compound of formula I to the compound of formula A is from 4:1 to 1:4.

6. The method of controlling pathogenic damage or pest damage in a plant propagation material, a plant, and/or plant organs that grow at a later point in time, which comprises applying a composition according to claim 1 to the plant propagation material.

7. A method of improving the growing characteristics of a plant, which comprises applying a composition according to claim 1 to a plant propagation material; and allowing the plant propagation material to grow into a plant.

* * * * *